United States Patent
Yamadoi et al.

(10) Patent No.: US 11,001,565 B2
(45) Date of Patent: May 11, 2021

(54) GLYCOLIDE PRODUCTION METHOD

(71) Applicant: Kureha Corporation, Tokyo (JP)

(72) Inventors: Yuta Yamadoi, Tokyo (JP); Yoshinori Suzuki, Tokyo (JP); Takenori Tose, Tokyo (JP); Haruyasu Yamaji, Tokyo (JP); Toshihiko Ono, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 0 days.

(21) Appl. No.: 16/980,908

(22) PCT Filed: Feb. 20, 2019

(86) PCT No.: PCT/JP2019/006278
§ 371 (c)(1),
(2) Date: Sep. 15, 2020

(87) PCT Pub. No.: WO2019/181340
PCT Pub. Date: Sep. 26, 2019

(65) Prior Publication Data
US 2021/0002248 A1    Jan. 7, 2021

(30) Foreign Application Priority Data
Mar. 20, 2018    (JP) .............................. JP2018-052281

(51) Int. Cl.
*C07D 319/12*    (2006.01)
*B01J 23/745*    (2006.01)
*B01J 35/02*    (2006.01)

(52) U.S. Cl.
CPC .......... *C07D 319/12* (2013.01); *B01J 23/745* (2013.01); *B01J 35/02* (2013.01)

(58) Field of Classification Search
CPC ........ C07D 319/12; B01J 23/745; B01J 35/02
USPC ........................................................ 549/274
See application file for complete search history.

(56) References Cited

U.S. PATENT DOCUMENTS

2004/0087805 A1    5/2004    Yamane et al.

FOREIGN PATENT DOCUMENTS

| CN | 1496359 A | 5/2004 |
|---|---|---|
| CN | 101054371 A | 10/2007 |
| CN | 107151238 A | 9/2017 |
| FI | 980839 A | 10/1999 |
| JP | H8-119961 A | 5/1996 |
| JP | 2004-519485 A | 7/2004 |
| JP | 2006-104138 A | 4/2006 |

OTHER PUBLICATIONS

International Search Report of the International Searching Authority for PCT/JP2019/006278 dated May 14, 2019.
English translation of International Search Report of the International Searching Authority for PCT/JP2019/006278 dated May 14, 2019.
Written Opinion of the International Searching Authority for PCT/JP2019/006278 dated May 14, 2019.
English translation of Written Opinion of the International Searching Authority for PCT/JP2019/006278 dated May 14, 2019.
International Preliminary Report on Patentability (Chapter I) for PCT/JP2019/006278 dated Sep. 22, 2020.
English translation of the International Preliminary Report on Patentability (Chapter I) for PCT/JP2019/006278 dated Sep. 22, 2020.
Office Action dated Nov. 24, 2020 for Chinese Patent Application No. 201980014078.X.

*Primary Examiner* — Taylor V Oh
(74) *Attorney, Agent, or Firm* — Birch, Stewart, Kolasch & Birch, LLP

(57) ABSTRACT

The object of the present invention is to provide a glycolide production method capable of further increasing the production rate of glycolide. The glycolide production method according to the present invention includes adding metal iron to an aqueous glycolic acid solution, subjecting glycolic acid contained in the aqueous glycolic acid solution to which the metal iron is added, to dehydrating polycondensation to obtain a glycolic acid oligomer, and heating and depolymerizing the glycolic acid oligomer to obtain glycolide.

6 Claims, No Drawings

GLYCOLIDE PRODUCTION METHOD

TECHNICAL FIELD

The present invention relates to a method for producing glycolide.

BACKGROUND ART

Polyglycolic acid is a resin material that excels in biodegradability, gas barrier properties, and strength, and is used in a wide range of technical fields such as in sutures, artificial skin, and other polymer materials for medical purposes, bottles, films, and other packaging materials, and resin materials for various industrial products such as injection molded products, fibers, vapor deposition films, and fishing lines.

Such polyglycolic acids are required to have a high degree of polymerization according to the application. A polyglycolic acid with a high degree of polymerization can be produced by a method of subjecting glycolide to ring-opening polymerization. Furthermore, a reduction of the production costs of polyglycolic acid is demanded, and there is also a demand for the mass production of glycolide used as a raw material, that is, there is a demand to enable the production of glycolide at a high production rate.

The glycolide that is a raw material of polyglycolic acid can be produced through 1) subjecting glycolic acid to dehydrating polycondensation to obtain a glycolic acid oligomer (dehydrating polycondensation), and 2) depolymerizing the obtained glycolic acid oligomer (depolymerization).

Methods of depolymerizing glycolic acid oligomers in the presence of a stabilizer such as iron sulfate in order to stably produce glycolide are known (for example, Patent Document 1). When depolymerization is carried out in the presence of a stabilizer such as iron sulfate in this manner, it is said that the stabilizer such as iron sulfate traps alkali metal ions mixed in the reaction system and stabilizes the depolymerization reaction.

CITATION LIST

Patent Document

Patent Document 1: JP 2004-519485 T

SUMMARY OF INVENTION

Technical Problem

Glycolide can be favorably produced with the glycolide production method described in Patent Document 1. However, from the perspective of reducing the cost to produce polyglycolic acid having a high degree of polymerization, there is a demand to further improve the production rate of the glycolide that is used as a raw material.

In light of the foregoing, an object of the present invention is to provide a glycolide production method that can further increase the production rate of glycolide.

Solution to Problem

The glycolide production method according to the present invention includes: adding metal iron to an aqueous glycolic acid solution; subjecting the glycolic acid contained in the aqueous glycolic acid solution to which the metal iron is added, to dehydrating polycondensation to obtain a glycolic acid oligomer; and heating and depolymerizing the glycolic acid oligomer to obtain glycolide.

Advantageous Effects of Invention

According to the present invention, a glycolide production method capable of further increasing the production rate of glycolide can be provided.

DESCRIPTION OF EMBODIMENTS

The present inventors focused on the addition of metal iron as a catalyst to increase the production rate of glycolide. In particular, it is generally thought that a catalyst should be added in the depolymerization to increase the production rate of glycolide. The depolymerization is typically carried out in an organic solvent from the perspective of being able to stably produce glycolide in large quantities. However, since the metal iron does not dissolve in an organic solvent, even when added in the depolymerization, the metal iron cannot be dissolved in the organic solvent, and thus it is not possible to effectively exhibit the action of the metal iron.

In contrast, in the present invention, metal iron is added to the aqueous glycolic acid solution used in the dehydrating polycondensation. As a result, the metal iron can be favorably dissolved and dispersed in the aqueous glycolic acid solution, and therefore iron ions can be favorably dispersed in the obtained glycolic acid oligomer. Through this, it is thought that even in the depolymerization, the iron ions can favorably act as a catalyst during the depolymerization reaction because a state in which the iron ions are favorably dispersed in the glycolic acid oligomer can be maintained. It is also thought that in the dehydrating polycondensation, the iron ions may act as a catalyst during the dehydrating polycondensation reaction. In other words, it is thought that in both the dehydrating polycondensation reaction and the depolymerization reaction, the iron ions favorably act as a catalyst, and as a result the production rate of glycolide is dramatically increased.

It is also thought that when dissolved in an aqueous solution, metal iron exhibits high activity because unlike iron sulfate and the like, the metal iron is not affected by ligands. Therefore, it is thought that the production rate of glycolide can be favorably increased even at low addition amounts of the metal iron. The present invention was completed based on these findings.

1. Glycolide Production Method

The glycolide production method according to an embodiment of the present invention includes: 1) adding metal iron to an aqueous glycolic acid solution (metal iron addition), 2) subjecting the glycolic acid contained in the aqueous glycolic acid solution to which the metal iron is added, to dehydrating polycondensation to obtain a glycolic acid oligomer (dehydrating polycondensation), and 3) heating and depolymerizing the obtained glycolic acid oligomer to obtain glycolide (depolymerization).

Step 1) Metal Iron Addition

Metal iron is added to an aqueous glycolic acid solution. The metal iron is thereby dissolved in the aqueous glycolic acid solution.

The aqueous glycolic acid solution is an aqueous solution containing glycolic acid. The glycolic acid may be an ester (for example, a lower alkyl ester), a salt (for example, a sodium salt), or the like.

The content of glycolic acid with respect to the total mass of the aqueous glycolic acid solution is, for example, from 1 mass % to 99 mass %, and more preferably from 50 mass % to 90 mass %.

As the aqueous glycolic acid solution, a high-purity aqueous glycolic acid solution having a low content of impurities such as organic material and metal ions is preferably used in order to facilitate production of high purity glycolide.

The metal iron is iron that may contain components other than iron, but from the perspective of suppressing unnecessary reactions of components other than iron, the content of the components other than iron is preferably 10 mass % or less. The form of the metal iron may be any form that can be fed into the reactor, and the metal iron may be a powder, may be plate shaped, may be a wire shape (such as wound into a reel shape or the like), or may be a lump shape. Among these, from the perspective of facilitating uniform dispersion in the aqueous glycolic acid solution, the metal iron is preferably a powder, that is, an iron powder.

The average particle size of the iron powder is not particularly limited, but, for example, from the perspective of facilitating uniform dispersion in the aqueous glycolic acid solution, the iron powder is preferably fine and has an average particle size of preferably from 1 μm to 1000 μm, more preferably from 1 μm to 500 μm, and even more preferably from 1 μm to 50 μm. The average particle size of the iron powder can be measured from an arithmetic mean of the volume average particle size distribution using a particle size distribution measurement device.

The addition amount of the metal iron is not particularly limited, but the addition amount is preferably from 10 ppm to 1000 ppm, more preferably from 30 ppm to 700 ppm, and even more preferably from 100 ppm to 500 ppm with respect to the total mass of the glycolic acid. When the addition amount of the metal iron is a certain amount or greater, the rate of the dehydrating polycondensation reaction of the glycolic acid and the rate of the depolymerization reaction of the glycolic acid oligomer are easily increased, and as a result, the production rate of glycolide tends to increase. When the addition amount of the metal iron is a certain amount or less, the remaining amount of undissolved metal iron is easily reduced, thereby facilitating a reduction in recovery costs.

From the perspective of facilitating a uniform dissolution of the metal iron, the metal iron may be added while heating the aqueous glycolic acid solution. From a similar perspective, the metal iron may be added while stirring the aqueous glycolic acid solution.

The metal iron addition may be performed before step 2) or simultaneously with step 2). In a case where the metal iron addition and step 2) are performed simultaneously, when the metal iron is to be added, the aqueous glycolic acid solution is heated, and at least a portion of the glycolic acid may be polycondensed.

Step 2) Dehydrating Polycondensation

The glycolic acid contained in the aqueous glycolic acid solution obtained in step 1) described above is subjected to dehydrating polycondensation to obtain glycolic acid oligomers. More specifically, the aqueous glycolic acid solution is heated until the distillation of low molecular weight substances such as water and alcohol is substantially completed, and the glycolic acid is subjected to polycondensation.

The heating temperature during the dehydrating polycondensation reaction (dehydrating polycondensation temperature) is preferably from 50° C. to 300° C., more preferably from 100° C. to 250° C., and even more preferably from 140° C. to 230° C.

After the dehydrating polycondensation reaction is completed, the produced glycolic acid oligomer can be used as is as a raw material for step 3) (depolymerization) described below.

The weight average molecular weight (Mw) of the obtained glycolic acid oligomer is preferably from 1000 to 100000, and more preferably from 10000 to 100000, from the perspective of glycolide yield. The weight average molecular weight (Mw) can be measured by gel permeation chromatography (GPC).

From the perspective of the yield of glycolide for the depolymerization reaction, the melting point (Tm) of the obtained glycolic acid oligomer is, for example, preferably 140° C. or higher, more preferably 160° C. or higher, and even more preferably 180° C. or higher. The upper limit of the melting point (Tm) of the glycolic acid oligomer is, for example, 220° C. Here, the melting point (Tm) of the glycolic acid oligomer can be measured from the endothermic peak temperature when the glycolic acid oligomer is heated at a rate of 10° C./min in an inert gas atmosphere using a differential scanning calorimeter (DSC).

Step 3) Depolymerization

In this step, the glycolic acid oligomer obtained in the step 2) described above is heated and depolymerized to obtain glycolide. More specifically, the glycolic acid oligomer is depolymerized in an organic solvent, and glycolide is obtained.

First, the glycolic acid oligomer is added to an organic solvent to be described below, and heated under normal pressure or under reduced pressure to dissolve the glycolic acid oligomer in the organic solvent.

Organic Solvent

From the perspective of appropriately increasing the depolymerization reaction temperature and facilitating an increase in the production rate of glycolide, the organic solvent is a high boiling point organic solvent having a boiling point of from 230° C. to 450° C., preferably from 235° C. to 450° C., more preferably from 255° C. to 430° C., and even more preferably from 280° C. to 420° C.

Examples of such high boiling point organic solvents include aromatic dicarboxylic acid diesters, aromatic carboxylic acid esters, aliphatic dicarboxylic acid diesters, polyalkylene glycol diethers, aromatic dicarboxylic acid dialkoxyalkyl esters, aliphatic dicarboxylic acid dialkoxyalkyl esters, polyalkylene glycol diesters, and aromatic phosphoric acid esters. Among these, aromatic dicarboxylic acid diesters, aromatic carboxylic acid esters, aliphatic dicarboxylic acid diesters, and polyalkylene glycol diethers are preferable, and from the perspective of being less likely to cause thermal degradation, a polyalkylene glycol diether is more preferable.

As the polyalkylene glycol diether, a polyalkylene glycol diether represented by Formula (1) below is preferable.

[Chemical Formula 1]

$$X-O-(-R-O-)_p-Y \qquad (1)$$

In Formula (1), R denotes a methylene group or a linear or branched alkylene group having from 2 to 8 carbons. X and Y each denote an alkyl group or an aryl group having from 2 to 20 carbons, and p is an integer from 1 to 5. When p is 2 or greater, the plurality of R moieties may be mutually the same or different.

Examples of polyalkylene glycol diethers include polyalkylene glycol dialkyl ether, polyalkylene glycol alkyl aryl ether, and polyalkylene glycol diaryl ether.

Examples of polyalkylene glycol dialkyl ethers include diethylene glycol dialkyl ethers such as diethylene glycol dibutyl ether, diethylene glycol dihexyl ether, diethylene glycol dioctyl ether, diethylene glycol butyl-2-chlorophenyl ether, diethylene glycol butylhexyl ether, diethylene glycol butyloctyl ether, and diethylene glycol hexyloctyl ether; triethylene glycol dialkyl ethers such as triethylene glycol diethyl ether, triethylene glycol dipropyl ether, triethylene glycol dibutyl ether, triethylene glycol dihexyl ether, triethylene glycol dioctyl ether, triethylene glycol butyloctyl ether, triethylene glycol butyldecyl ether, triethylene glycol butylhexyl ether, and triethylene glycol hexyloctyl ether; polyethylene glycol dialkyl ethers such as tetraethylene glycol diethyl ether, tetraethylene glycol dipropyl ether, tetraethylene glycol dibutyl ether, tetraethylene glycol dihexyl ether, tetraethylene glycol dioctyl ether, tetraethylene glycol butylhexyl ether, tetraethylene glycol butyloctyl ether, tetraethylene glycol hexyloctyl ether, and other such tetraethylene glycol dialkyl ethers; and polypropylene glycol dialkyl ethers for which the ethyleneoxy group in the polyalkylene glycol dialkyl ether is substituted with a propyleneoxy group, and polybutylene glycol dialkyl ethers for which the ethyleneoxy group in the polyalkylene glycol dialkyl ether is substituted with a butyleneoxy group.

Examples of polyalkylene glycol alkyl aryl ethers include diethylene glycol butylphenyl ether, diethylene glycol hexylphenyl ether, diethylene glycol octylphenyl ether, triethylene glycol butylphenyl ether, triethylene glycol hexylphenyl ether, triethylene glycol octylphenyl ether, tetraethylene glycol butylphenyl ether, tetraethylene glycol hexylphenyl ether, tetraethylene glycol octylphenyl ether, and polyethylene glycol alkyl aryl ethers for which some of the hydrogen atoms on the phenyl group of these compounds are substituted with an alkyl group, an alkoxy group, or a halogen atom; and a polypropylene glycol alkyl aryl ether for which the ethyleneoxy group in the polyalkylene glycol alkyl aryl ether is substituted with a propyleneoxy group, and a polybutylene glycol alkyl aryl ether for which the ethyleneoxy group in the polyalkylene glycol alkyl aryl ether is substituted with a butyleneoxy group.

Examples of the polyalkylene glycol diaryl ethers include diethylene glycol diphenyl ether, triethylene glycol diphenyl ether, tetraethylene glycol diphenyl ether, or a polyethylene glycol diaryl ether for which some of the hydrogen atoms on the phenyl group of these compounds are substituted with an alkyl group, an alkoxy group, or a halogen atom; and a polypropylene glycol diaryl ether for which the ethyleneoxy group in the polyalkylene glycol diaryl ether is substituted with a propyleneoxy group, and a polybutylene glycol diaryl ether for which the ethyleneoxy group in the polyalkylene glycol diaryl ether is substituted with a butyleneoxy group.

Among these, from perspective of thermal degradation being less likely to occur, a polyalkylene glycol dialkyl ether is preferable, and tetraethylene glycol dibutyl ether, triethylene glycol butyloctyl ether, diethylene glycol dibutyl ether, and diethylene glycol butyl-2-chlorophenyl ether are more preferable, and from the perspective of the glycolide recovery ratio, tetraethylene glycol dibutyl ether and triethylene glycol butyloctyl ether are even more preferable.

The amount of the organic solvent is, for example, preferably from 30 to 5000 parts by mass, more preferably from 50 to 2000 parts by mass, and even more preferably from 100 to 1000 parts by mass, per 100 parts by mass of the glycolic acid oligomer.

Furthermore, a solubilizing agent may be further added as necessary to increase the solubility of the glycolic acid oligomer in the organic solvent.

Solubilizing Agent

The solubilizing agent is preferably a non-basic organic compound having a boiling point of 180° C. or higher, such as a monohydric alcohol, a polyhydric alcohol, a phenol, a monovalent aliphatic carboxylic acid, a polyvalent aliphatic carboxylic acid, an aliphatic amide, an aliphatic imide, or a sulfonic acid. Among these, from the perspective of being able to easily obtain an effect of a solubilizing agent, a monohydric alcohol and a polyhydric alcohol are preferable.

The boiling point of the monohydric or polyhydric alcohol is preferably 200° C. or higher, more preferably 230° C. or higher, and particularly preferably 250° C. or higher.

Such monohydric alcohols are preferably polyalkylene glycol monoethers represented by Formula (2) below.

[Chemical Formula 2]

$$HO-(R^1-O)q\text{-}X^1 \qquad (2)$$

In Formula (2), $R^1$ denotes a methylene group or a linear or branched alkylene group having from 2 to 8 carbons. $X^1$ denotes a hydrocarbon group. The hydrocarbon group is preferably an alkyl group. q is an integer of 1 or greater, and when q is 2 or greater, the plurality of $R^1$ moieties may be mutually the same or different.

Examples of polyalkylene glycol monoethers include polyethylene glycol monoethers such as polyethylene glycol monomethyl ether, polyethylene glycol monoethyl ether, polyethylene glycol monopropyl ether, polyethylene glycol monobutyl ether, polyethylene glycol monohexyl ether, polyethylene glycol monooctyl ether, polyethylene glycol monodecyl ether, and polyethylene glycol monolauryl ether; a polypropylene glycol monoether for which an ethyleneoxy group in the polyethylene glycol monoether is substituted with a propyleneoxy group, and a polybutylene glycol monoether for which an ethyleneoxy group in the polyethylene glycol monoether is substituted with a butyleneoxy group. Among these, a polyalkylene glycol monoether having from 1 to 18 and preferably from 6 to 18 carbons in the alkyl group included in the ether group is preferable, and a polyethylene glycol monoalkyl ether such as triethylene glycol monooctyl ether is more preferable.

Since the polyalkylene glycol monoether can increase the solubility of the glycolic acid oligomer, the use of a polyalkylene glycol monoether as a solubilizing agent facilitates a more rapid advancement of the depolymerization reaction of the glycolic acid oligomer.

Polyalkylene glycols represented by Formula (3) below are preferable as the polyhydric alcohols.

[Chemical Formula 3]

$$HO-(R^2-O)r\text{-}H \qquad (3)$$

In Formula (3), $R^2$ denotes a methylene group or a linear or branched alkylene group having from 2 to 8 carbons. r is an integer of 1 or greater, and when r is 2 or greater, the plurality of $R^2$ moieties may be mutually the same or different.

Examples of polyalkylene glycols include polyethylene glycol, polypropylene glycol, and polybutylene glycol.

The addition amount of the solubilizing agent is preferably from 0.1 to 500 parts by mass, and more preferably from 1 to 300 parts by mass, per 100 parts by mass of the glycolic acid oligomer. When the addition amount of the solubilizing agent is a certain amount or greater, the solubility of the glycolic acid oligomer in the organic solvent can be sufficiently enhanced, and when the addition amount is a certain amount or less, the cost required to recover the solubilizing agent can be reduced.

Next, while the obtained solution is heated under normal pressure or under reduced pressure, the glycolic acid oligomer is depolymerized.

The heating temperature during the depolymerization reaction (depolymerization temperature) may be equal to or higher than the temperature at which depolymerization of the glycolic acid oligomer occurs, and while the heating temperature depends on the degree of depressurization, the type of high boiling point organic solvent, and the like, the heating temperature is generally 200° C. or higher, preferably from 200° C. to 350° C., more preferably from 210° C. to 310° C., even more preferably from 220° C. to 300° C., and yet even more preferably from 230° C. to 290° C.

Heating during the depolymerization reaction is preferably performed under normal pressure or under reduced pressure, and is preferably performed under a reduced pressure from 0.1 kPa to 90 kPa. This is because the depolymerization reaction temperature decreases as the pressure is reduced, and therefore a lower pressure facilitates a reduction in the heating temperature, and the recovery ratio of the solvent is increased. The degree of depressurization is preferably from 1 kPa to 60 kPa, more preferably from 1.5 kPa to 40 kPa, and even more preferably from 2 kPa to 30 kPa.

Next, the produced glycolide is distilled out of the depolymerization reaction system along with the organic solvent. By distilling out the produced glycolide along with the organic solvent, adherence and accumulation of the glycolide on wall surfaces of the reaction vessel and lines can be prevented.

Glycolide is then recovered from the obtained distillate. Specifically, the distillate is cooled and phase separated, and glycolide is precipitated. The precipitated glycolide is separated and recovered from the mother liquor by a method such as filtration, centrifugal sedimentation, or decantation.

The mother liquor from which the glycolide has been separated may be recycled and used as is without purification, or may be recycled and used after being treated with activated carbon and filtered and purified, or after being purified through distillation once again.

When the glycolide is distilled out together with the organic solvent, the volume of the depolymerization reaction system decreases. In contrast, the depolymerization reaction can be performed continuously or repeatedly for a long period of time by adding, to the depolymerization reaction system, a glycolic acid oligomer and an organic solvent in an amount equivalent to the amount that was distilled away.

As described above, in an embodiment of the present invention, metal iron is added to an aqueous glycolic acid solution to carry out a dehydrating polycondensation reaction and a depolymerization reaction. As a result, the production rate of glycolide can be dramatically increased.

2. Glycolide

The glycolide (also referred to as crude glycolide) obtained by the production method of an embodiment of the present invention is preferably high in purity. Specifically, the purity of the glycolide is preferably not less than 80%, more preferably not less than 90%, and even more preferably not less than 95%. Thus, according to the glycolide production method of an embodiment of the present invention, high purity glycolide can be obtained at a high production rate.

EXAMPLES

The present invention will be described in further detail below with reference to examples. The scope of the present invention is not to be construed as being limited by these examples.

Example 1

A separable flask having a volume of 1 L was charged with 1.3 kg of a 70 mass % glycolic acid aqueous solution (available from The Chemours Company, high purity grade), and 26 mg of iron powder (iron content of 29 ppm with respect to the glycolic acid, average particle size of 20 μm) was added (step 1 described above). Note that the average particle size of the iron powder was measured from an arithmetic mean of the volume average particle size distribution using a particle size distribution measurement device.

Next, the mixture was heated under stirring at normal pressure to increase the temperature from room temperature to 215° C., and a polycondensation reaction was carried out while distilling away the water produced. Next, the pressure inside the flask was gradually reduced from normal pressure to 3 kPa, after which the contents in the flask were heated at 215° C. for 3 hours, low-boiling substances such as unreacted raw materials were distilled away, and a glycolic acid oligomer (weight average molecular weight (Mw) of 22000) was obtained (step 2 described above).

Next, 120 g of the obtained glycolic acid oligomer, 130 g of tetraethylene glycol dibutyl ether, and 100 g of octyltriethylene glycol were added to a reactor having a volume of 0.5 L, and then heated to 235° C., and the reaction system was formed into a homogeneous solution. While this reaction system was heated at a temperature of 235° C. under stirring at a speed of 170 rpm, a depolymerization reaction was carried out for 12 hours under a reduced pressure of 3 kPa (step 3 described above). During the reaction, every one hour, tetraethylene glycol dibutyl ether and crude glycolide were co-distilled, the crude glycolide was separated and recovered from the co-distillate, and the mass was measured. Along with the recovery of crude glycolide every one hour, a glycolic acid oligomer in an amount equivalent to the mass of the recovered crude glycolide was fed into the reaction system. The amount of crude glycolide recovered per hour was arithmetically averaged to obtain the production rate (g/h) of the crude glycolide.

Example 2

The crude glycolide production rate was determined in the same manner as in Example 1 with the exception that the addition amount of iron powder was changed to 195 mg (iron content relative to glycolic acid was 214 ppm).

Example 3

The crude glycolide production rate was determined in the same manner as in Example 1 with the exception that the addition amount of iron powder was changed to 325 mg (iron content relative to glycolic acid was 357 ppm).

Comparative Example 1

The crude glycolide production rate was determined in the same manner as in Example 1 with the exception that iron powder was not added.

Comparative Example 2

The crude glycolide production rate was determined in the same manner as in Example 1 with the exception that 130 mg of iron sulfate • n-hydrate (iron content relative to glycolic acid was 29 ppm) was added instead of the iron powder.

The evaluation results for each of Examples 1 to 3 and Comparative Examples 1 and 2 are shown in Table 1.

TABLE 1

|  | Additive | Iron Content Relative to Glycolic Acid (ppm) | Crude Glycolide Production Rate (g/h) |
|---|---|---|---|
| Example 1 | Iron powder | 29 | 18.2 |
| Example 2 |  | 214 | 20.7 |
| Example 3 |  | 357 | 22.3 |
| Comparative Example 1 | — | — | 13.2 |
| Comparative Example 2 | $Fe_2(SO_4)_3$ | 29 | 16.4 |

As shown in Table 1, in Examples 1 to 3 in which iron powder was added, the production rate of crude glycolide was higher than that of Comparative Example 1 in which iron powder was not added and Comparative Example 2 in which iron sulfate was added.

Furthermore, the results indicate that as the addition amount of iron powder is increased, the production rate of crude glycolide further increases (from a comparison of Examples 1 to 3).

The present application claims priority to JP 2018-052281 filed on Mar. 20, 2018. The contents described in the specification of said application are all incorporated herein by reference.

INDUSTRIAL APPLICABILITY

According to the present invention, a glycolide production method capable of further increasing the production rate of glycolide can be provided.

The invention claimed is:

1. A glycolide production method comprising:
adding a metal iron to an aqueous glycolic acid solution;
subjecting glycolic acid contained in the aqueous glycolic acid solution to which the metal iron is added, to dehydrating polycondensation to obtain a glycolic acid oligomer; and
heating and depolymerizing the glycolic acid oligomer to obtain glycolide,
wherein the metal iron consists essentially of elemental iron.

2. The glycolide production method according to claim 1, wherein an addition amount of the metal iron is from 10 ppm to 1000 ppm relative to a total mass of the glycolic acid.

3. The glycolide production method according to claim 1, wherein the metal iron is iron powder.

4. The glycolide production method according to claim 3, wherein an average particle size of the iron powder is from 1 μm to 1000 μm.

5. The glycolide production method according to claim 1, wherein a dehydrating polycondensation temperature is from 50° C. to 300° C.

6. The glycolide production method according to claim 1, wherein the depolymerization is carried out in the presence of a polyalkylene glycol ether represented by Formula (1):

[Chemical Formula 1]

$$X\text{—}O\text{—}(\text{—}R\text{—}O\text{—})_p\text{-}Y \qquad (1)$$

in Formula (1),
R is a methylene group, or a linear or branched alkylene group having from 2 to 8 carbons,
X and Y each independently denote an alkyl group or an aryl group having from 2 to 20 carbons,
p is an integer from 1 to 5, and
when p is 2 or greater, a plurality of R moieties may be the same or different.

\* \* \* \* \*